United States Patent [19]

Malone

[11] Patent Number: 5,070,093

[45] Date of Patent: Dec. 3, 1991

[54] TETRACYCLIC AMINES USEFUL AS CEREBROVASCULAR AGENTS

[75] Inventor: Thomas C. Malone, Canton, Mich.

[73] Assignee: Warner-Lambert Company, Morris Plains, N.J.

[21] Appl. No.: 677,029

[22] Filed: Mar. 28, 1991

Related U.S. Application Data

[62] Division of Ser. No. 565,306, Aug. 9, 1990.

[51] Int. Cl.$^5$ .................. C07D 209/56; C07D 223/14; C07D 215/02
[52] U.S. Cl. ...................................... 514/284; 546/75; 548/425; 540/481; 514/216; 514/286; 514/410
[58] Field of Search .......................... 546/75; 548/425; 514/284, 286, 410; 540/481

[56] References Cited

U.S. PATENT DOCUMENTS 3,840,557 10/1974 Yardley ............................... 548/425
3,980,641 9/1976 Monkovic ........................... 548/425

Primary Examiner—Mary C. Lee
Assistant Examiner—Peter Davis
Attorney, Agent, or Firm—Elizabeth M. Anderson

[57] ABSTRACT

A novel series of tetracyclic amines, methods of preparation, compositions containing the amines, and methods for using them in the treatment and/or prevention of cerebrovascular disorders are disclosed.

8 Claims, No Drawings

TETRACYCLIC AMINES USEFUL AS CEREBROVASCULAR AGENTS

This is a divisional application of U.S. Application Ser. No. 07/565,306 filed Aug. 9, 1990.

BACKGROUND OF THE INVENTION

Excessive excitation by neurotransmitters can cause the degeneration and death of neurons. It is believed that this degeneration is in part mediated by the excitotoxic actions of glutamate and aspartate at the N-methyl-D-aspartate (NMDA) receptor. This excitotoxic action is responsible for the loss of neurons in cerebrovascular disorders such as: cerebral ischemia or cerebral infraction resulting from a range of conditions such as thromboembolic or hemorrhagic stroke, cerebral vasospasm, hypoglycemia, cardiac arrest, status epilepticus, perinatal asphyxia, cerebral trauma and anoxia (such as from drowning and pulmonary surgery).

There are no specific therapies for these neurodegenerative diseases, however, compounds which act specifically as antagonists of the NMDA receptor complex, either competitively or noncompetitively, offer a novel therapeutic approach to these disorders: R. Schwarcz and B. Meldrum, *The Lancet* 140 (1985); B. Meldrum in "Neurotoxins and Their Pharmacological Implications" edited by P. Jenner, Raven Press, New York (1987); D. W. Choi, *Neuron* 1:623 (1988). Confirmation of the protective effects of noncompetitve NMDA antagonists in various pharmacological models of neurodegenerative disorders have appeared in the literature: J. W. McDonald, F. S. Silverstein, and M. V. Johnston, *Eur. J. Pharmocol.* 140:359 (1987); R. Gill, A. C. Foster, and G. N. Woodruff, *J. Neurosci.* 7:3343 (1987); S. M. Rothman, J. H. Thurston, R. E. Hauhart, G. D. Clark, and J. S. Soloman, *Neurosci.* 21:673 (1987); M. P. Goldbert, P-C. Pham, and D. W. Choi, *Neurosci. Lett.* 80:11 (1987); L. F. Copeland, P. A. Boxer, and F. W. Marcoux, *Soc. Neurosci. Abstr.* 14 (part 1):420 (1988); J. A. Kemp. A. C. Foster, R. Gill, and G. N. Woodruff, *TIPS* 8:414 (1987); R. Gill, A. C. Foster, and G. N. Woodruff, *J. Neurosci.* 25:847 (1988); C. K. Park, D. G. Nehls, D. I. Graham, G. M. Teasdale, and J. M. McCulloch, *Ann. Neurol.* 24:543 (1988); G. K. Steinburg, C. P. George, R. DeLaPlaz, D. K. Shibata, and T. Gross, *Stroke* 19:1112 (1988); J. F. Church, S. Zeman, and D. Lodge, *Anesthesiology* 69:702 (1988).

The compounds of the present invention are useful in the treatment of neurodegenerative disorders including cerebrovascular disorders. Such disorders include but are not limited to cerebral ischemia or cerebral infarction resulting from a range of conditions such as thromboembolic or hemorrhagic stroke, cerebral vasospasm, hypoglycemia, cardiac arrest, status epilepticus, perinatal asphyxia, cerebral trauma and anoxia such as from drowning and/or pulmonary surgery. Other treatments are for schizophrenia, epilepsy, spasticity, neurodegenerative disorders such as Alzheimer's disease or Huntington's disease, Olivo-pontocerebellar atrophy, spinal cord injury, and poisoning by exogenous NMDA poisons (e.g., some forms of lathyrism). Further uses are as analgesics and anesthetics, particularly for use in surgical procedures where a finite risk of cerebrovascular damage exists.

SUMMARY OF THE INVENTION

The present invention concerns compounds of the formula I

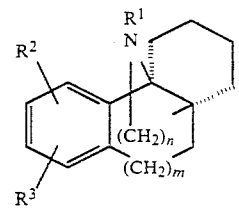

or a pharmaceutically acceptable acid addition salt thereof wherein $R^1$, $R^2$, $R^3$, m, and n are as described herein below.

The present invention also includes a pharmaceutical composition comprising a therapeutically effective amount of a compound of formula I together with a pharmaceutically acceptable carrier.

The present invention also includes a method for treating cerebrovascular disorders which comprises administering to a patient in need thereof the above pharmaceutical composition in unit dosage form.

The present invention also includes a method of treating disorders responsive to the blockade of glutamic and aspartic acid receptors in a patient comprising administering a therapeutically effective amount of the above composition.

The invention also includes a method for treating cerebral ischemia, cerebral infarction, cerebral vasospasm, hypoglycemia, cardiac arrest, status epilepticus, cerebral trauma, schizophrenia, epilepsy, neurodegenerative disorders, Alzheimer's disease, or Huntington's disease comprising administering to a patient in need thereof a therapeutically effective amount of the above composition.

The invention also includes a method for treating stroke in patients in need thereof which comprises administering to a patient in need thereof a therapeutically effective amount of the above composition.

The invention also includes using as an anesthetic the above composition in surgical operations where a risk of cerebrovascular damage exists.

The invention further includes processes for the preparation of compounds of formula I.

The invention still further includes novel intermediates useful in the processes.

DETAILED DESCRIPTION

The present invention concerns compounds of the formula

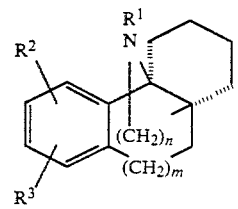

or a pharmaceutically acceptable acid addition salt thereof wherein:

R¹ is hydrogen, lower alkyl, lower alkenyl, lower alkynyl, arylloweralkyl, cyclopropylloweralkyl, or a pharmaceutically acceptable labile group;

R² and R³ are each independently hydrogen, lower alkyl, hydroxy, lower alkoxy, halogen, amino, monoloweralkylamino, diloweralkylamino;

m is an integer of from 0 to 2; and n is an integer of from 2 to 4.

Preferred compounds of the instant invention are those of formula I wherein:

R¹ is hydrogen, lower alkyl, lower alkenyl, cyclopropylmethyl or arylloweralkyl;

R² and R³ are independently hydrogen, lower alkyl, hydroxy, or lower alkoxy;

m is an integer of 0 or 1;

n is 2 or 3; and indicates the ring is cis relative to its attachment at to the molecule.

More preferred compounds of the instant invention are those of formula I wherein:

R¹ is hydrogen, lower alkyl, cyclopropylmethyl, or arylloweralkyl;

R² and R³ are independently hydrogen, hydroxy, or lower alkoxy;

m is an integer 0 or 1; and n is an integer 2 or 3.

Still more preferred are compounds of formula I wherein:

R¹ is hydrogen, methyl, ethyl, propyl, allyl, cyclopropylmethyl, or benzyl;

R² and R³ are each independently hydrogen, methoxy, or hydroxy;

m is the integer 0 or 1; and n is the integer 2 or 3.

Other more preferred compounds of the instant invention include:

(+), (−), or (±)-2,3-Dihydro-1H,4H-3a,8b-butanoindeno[1,2-b]pyrrole, (+), (−), or (±)-2,3-Dihydro-7-methoxy-1H,4H-3a,8b-butanoindeno[1,2-b]pyrrole, (+), (−), or (±)-2,3-Dihydro-1-methyl-1H,4H-3a,8b-butanoindeno[1,2-b]pyrrole, (+), (−), or (±)-2,3-Dihydro-7-methoxy-1-methyl-1H,4H-3a,8b-butanoindeno[1,2-b]pyrrole, (+), (−) or (±)-2,3-Dihydro-7-methoxy-1-ethyl-1H,4H-3a,8b-butanoindeno[1,2-b]pyrrole, (+), (−), or (±)-2,3,4,5-tetrahydro-1-(2-propenyl)-3a,9b-butano-1H-benz[g]indole, (+), (−), or (±)-2,3,4,5-Tetrahydro-3a,9b-butano-1H-benz[g]indol-8-ol, (+), (−), or (±)-2,3,4,5-Tetrahydro-1-methyl-3a,9b-butano-1H-benz[g]indol-8-ol, (+), (−), or (±)-2,3-Dihydro-1H,4H-3a,8b-butanoindeno[1,2-b]pyrrol-7-ol, (+), (−), or (±)-2,3-Dihydro-1-methyl-1H,4H-3a,8b-butanoindeno[1,2-b]pyrrol-7-ol, (+) (−), or (±)-1,2,3,4,5,6-Hexahydro-4a,10b-butanobenz[h]quinoline, (+), (−), or (±)-1,2,3,4,5,6-Hexahydro-9-methoxy-4a,10b-butanobenz[h]quinoline, (+), (−), or (±)-1,2,3,4,-Tetrahydro-4a,9b-butano-5H-indeno[1,2-b]pyridine, (+), (−), or (±)-1,2,3,4,-Tetrahydro-8-methoxy-4a,9b-butano-5H-indeno[1,2-b]pyridine, (+), (−), or (±)-1,2,3,4,5,6-Hexahydro-1-methyl-4a,10b-butanobenz[h]quinoline, (+), (−), or (±)-1,2,3,4,5,6-Hexahydro-9-methoxy-1-methyl-4a,10b-butanobenz[h]quinoline, (+), (−), or (±)-1,2,3,4,-Tetrahydro-1-methyl-4a,9b-butano-5H-indeno[1,2-b]pyridine, (+), (−), or (±)-1,2,3,4,-Tetrahydro-8-methoxy-1-methyl-4a,9b-butano-5H-indeno[1,2-b]pyridine, (+), (−), or (±)-1,2,3,4,5,6-Hexahydro-4a,10b-butanobenz[h]quinolin-9-ol, (+), (−), or (±)-1,2,3,4,5,6-Hexahydro-1-methyl-4a,10b-butanobenz[h]quinolin-9-ol, (+), (−), or (±)-1,2,3,4-Tetrahydro-1a,9b-butano-5H-indeno[1,2-b]pyridin-8-ol, and (+), (−), or (±)-1,2,3,4-Tetrahydro-1-methyl-4a,9b-butano-5H-indeno[1,2-b]pyridin-8-ol.

Most preferred compounds of the instant invention are:

(+), (−), or (±)-2,3,4,5-Tetrahydro-3a,9b-butano-1H-benz[g]indole, (+), (−), or (±)-2,3,4,5-Tetrahydro-1-methyl-3a,9b-butano-1H-benz[g]indole, (+), (−), or (±)-2,3,4,5-Tetrahydro-1-ethyl-3a,9b-butano-1H-benz[g]indole, (+), (−), or (±)-2,3,4,5-Tetrahydro-1-propyl-3a,9b-butano-1H-benz[g]indole, (+), (−), or (±)-2,3,4,5-Tetrahydro-1-(cyclopropylmethyl)-3a,9b-butano-1H-benz[g]indole, (+), (−), or (±)-2,3,4,5-Tetrahydro-1-phenylmethyl-3a,9b-butano-1H-benz[g]indole, (+), (−), or (±)-2,3,4,5-Tetrahydro-8-methoxy-3a,9b-butano-1H-benz[g]indole, (+), (−), or (±)-2,3,4,5-Tetrahydro-8-methoxy-1-methyl-3a,9b-butano-1H-benz[g]indole, and (+), (−), or (±)-2,3,4,5-Tetrahydro-8-methoxy-1-ethyl-3a,9b-butano-1H-benz[g]indole.

Compounds of the instant invention include solvates, hydrates, and pharmaceutically acceptable salts of compounds of formula I above.

The compounds of the present invention contain asymmetric carbon atoms. The instant invention includes the individual enantiomers, which may be prepared or isolated by methods known in the art.

Any resulting racemates can be resolved into the optical antipodes by known methods, for example by separation of the diastereomeric salts thereof, with an optically active acid, and liberating the optically active amine compound by treatment with a base. Racemic compounds of the instant invention can thus be resolved into their optical antipodes e.g., by fractional crystallization of d- or l- (tartarates, mandelates, or camphorsulfonate) salts. The compounds of the instant invention may also be resolved into the optical antipodes by the formation of diastereomeric carbamates by reacting the compounds of the instant invention with an optically active chloroformate, for example (−)-menthyl chloroformate, or by the formation of a diastereomeric amide by reacting the compounds of the instant invention with an optically active activated carboxy acid such as that derived from (+) or (−) phenylalanine, (+) or (−) phenylglycine, (−)-camphanic acid or the like.

Additional methods for resolving optical isomers, known to those skilled in the art may be used, for example those discussed by J. Jaques, A. Collet, and S. Wilen in "Enantiomers, Racemates and Resolutions", John Wiley and Sons, New York (1981).

The term lower in connection with organic groups, radical or compounds includes up to and including seven members, preferably up to and including four and most preferably one, two, or three carbon atoms except as otherwise specifically described.

Lower alkyl means a straight or branched chain of from one to four carbon atoms including but not limited to methyl, ethyl, propyl, isopropyl, and butyl.

Lower alkenyl means a group from one to four carbon atoms, for example, but not limited to ethylene, 1,2- or 2,3-propylene, 1,2- 2,3-, or 3,4-butylene. Preferred is 2,3-propylene.

Lower alkynyl means a group from one to four carbon atoms, for example, but not limited to ethynyl, 2,3-propynyl, 2,3-, or 3,4-butynyl; propynyl is the preferred group.

Cyclopropylloweralkyl means cyclopropyl-$C_{1-4}$-alkyl, meaning for example, cyclopropylmethyl, 2-(cyclopropyl)ethyl, 3-(cyclopropyl)propyl; cyclopropylmethyl is the preferred group.

Lower alkoxy means a group of from one to four carbon atoms, for example, but not limited to methoxy, ethoxy, propoxy; methoxy is the preferred group.

Halogen is fluorine, chlorine, bromine, or iodine; fluorine, chlorine, and bromine are the preferred groups.

Arylloweralkyl means aryl-$C_{1-4}$-alkyl, meaning for example, benzyl, 2-phenylethyl, 3-phenylpropyl; preferred group is benzyl. The aryl groups may be substituted, for example, by lower alkyl, lower alkoxy, hydroxy, and halogen.

Monoloweralkylamino means a group containing from one to four carbon atoms, for example, but not limited to methylamino, ethylamino, n- or i-(propylamino or butylamino).

Diloweralkylamino means a group containing from one to four carbon atoms in each lower alkyl group, for example, but not limited to dimethylamino, diethylamino, di-(n-propyl)-amino, di-(n-butyl)-amino, or may represent a fused ring, for example piperidine.

Physiologically labile group includes but is not limited to such derivatives described by; I. H. Pitman in *Med. Chem. Rev.* 2:189 (1981); J. Alexander, R. Cargill, S. R. Michelson and H. Schwam in *J. Med. Chem.* 31:318 (1988); V. H. Naringrekar and V. J. Stella in European Patent Application 214,009-A2 and include certain amides, such as amides of amino acids, for example glycine, or serine, enaminone derivatives and (acyloxy)alkylcarbamates.

Well-known protecting groups and their introduction and removal are described, for example, in J. F. W. McOmie, *Protective Groups in Organic Chemistry*, Plenum Press, London, New York (1973), and T. W. Greene, *Protective Groups in Organic Synthesis*, Wiley, New York (1981).

Salts of the compounds of the invention are preferably pharmaceutically acceptable salts. The compounds of the invention are basic amines from which acid addition salts of pharmaceutically acceptable inorganic or organic acids such as strong mineral acids, for example, hydrohalic, e.g., hydrochloric or hydrobromic acid; sulfuric, phosphoric or nitric acid; aliphatic or aromatic carboxylic or sulfonic acids, e.g., acetic, propionic, succinic, glycolic, lactic, malic, tartaric, gluconic, citric, ascorbic, maleic, fumaric, pyruvic, pamoic, nicotinic, methanesulfonic, ethanesulfonic, hydroxyethanesulfonic, benzenesulfonic, p-toluenesulfonic, or napthlenesulfonic acid can be prepared.

For isolation or purification purposes, salts may be obtained which might not be useful for pharmaceutical purposes. Pharmaceutically acceptable salts useful for therapeutic purposes are preferred.

The present invention also includes processes for making the compounds of formula I above.

One process for the preparation of compounds of formula I is illustrated in Scheme A below.

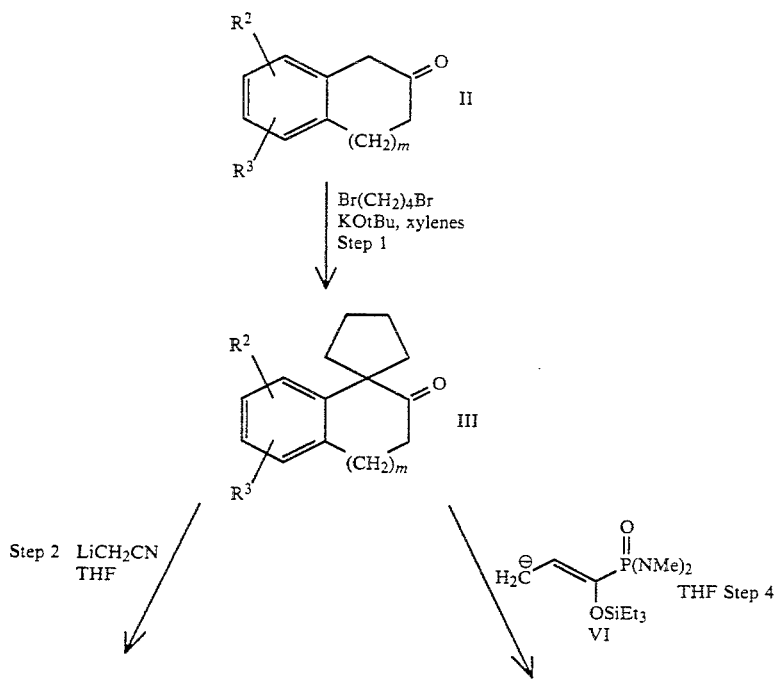

SCHEME A

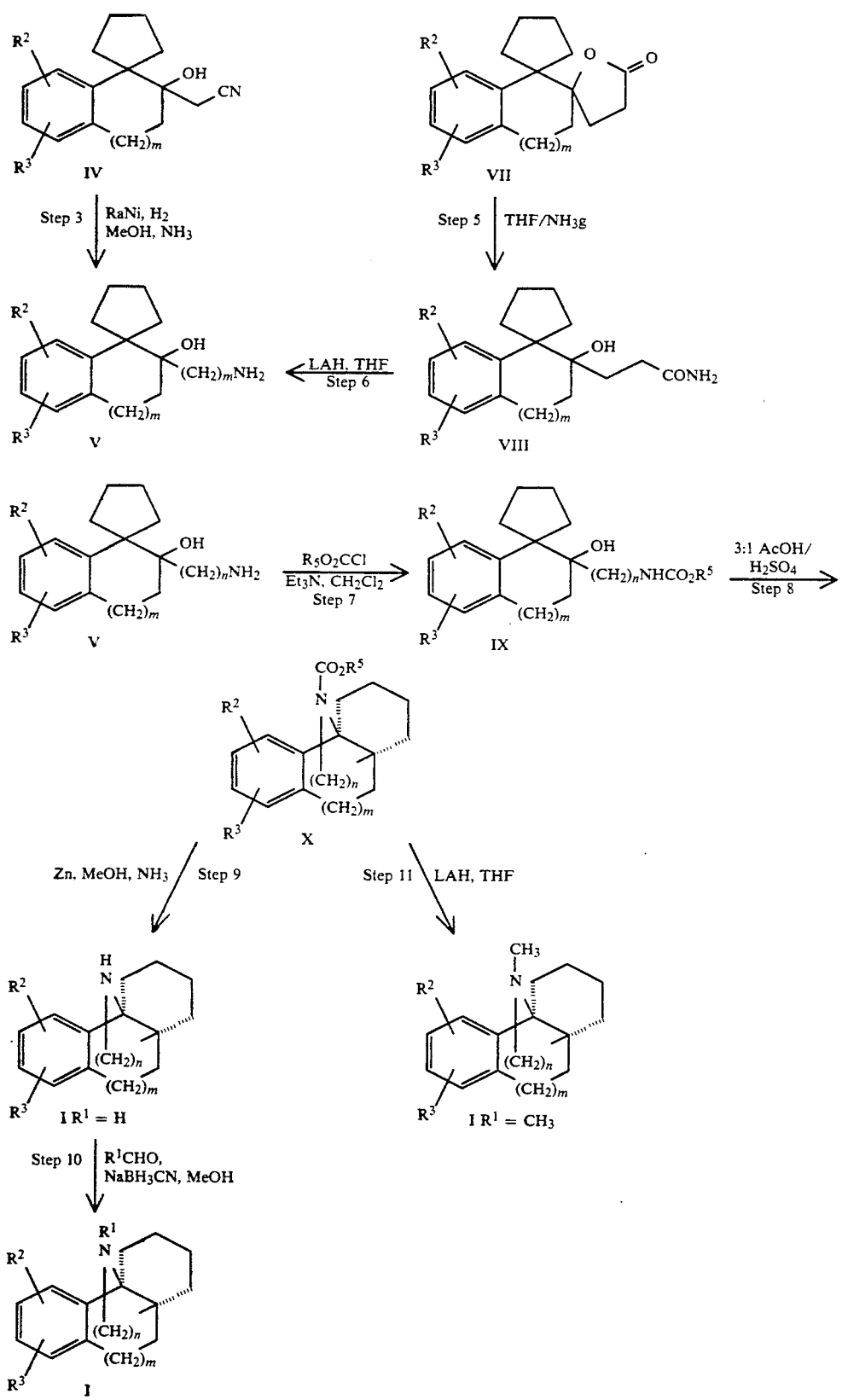
Step (1) The compound of formula II wherein m is 0 or 1

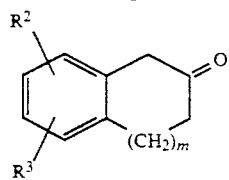

II and $R^2$ and $R^3$ are as previously defined are treated with 1,4-dibromobutane under conditions described in *Bull. Soc. Chim. France* 346 (1957) to give the compounds of the formula III.

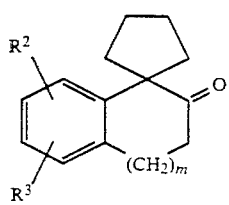

III

Step (2) The compounds of the formula III are treated with lithioacetonitrile, in a solvent such as ether, tetrahydrofuran, or the like, at a temperature between $-78°$ C. and $20°$ C. to afford the compounds of the formula IV.

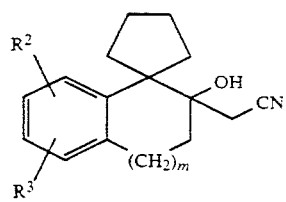

IV

Step (3) The compounds of the formula IV are hydrogenated in the presence of a catalyst such as Raney Nickel, or the like, in a solvent such as methanol or ethanol containing ammonia, under a hydrogen atmosphere to give the compounds of the formula V wherein n is 2.

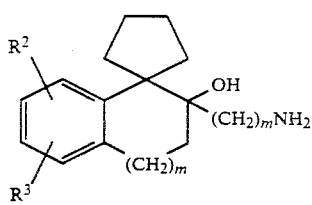

V

Step (4) Alternatively, the compounds of the formula III are treated with a compound of the formula VI

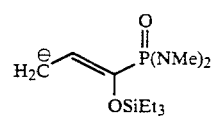

VI under conditions described by Evans et al in *J. Amer. Chem Soc.* 371, (1979) or by other methods known to those skilled in the art, such as those described in *Tetrahedron* 205, (1983) to give the compounds of the formula VII.

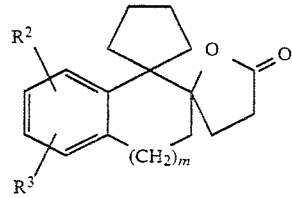

VII

Step (5) The compounds of the formula VII are treated with ammonia in a solvent such as toluene, tetrahydrofuran, or the like to give the compounds of the formula VIII.

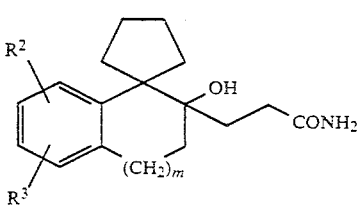

VIII

Step (6) The compounds of the formula VIII are reduced using lithium aluminum hydride, diborane, or the like, in a solvent such as ether, tetrahydrofuran, or the like to give the compounds of the formula V wherein n is 3.

Step (7) The compounds of the formula V are treated with methyl chloroformate, ethyl chloroformate, 2,2,2-trichloroethyl chloroformate or an optically active chloroformate, for example (−)-menthyl chloroformate, (−)-α-methylbenzyl chloroformate or the like, in the presence of a trialkylamine such as triethylamine, tributylamine, diisopropylethylamine or the like, in a solvent such as dichloromethane, chloroform, or the like, to give the compounds of the formula IX wherein $R^5$ is methyl, ethyl, 2,2,2-trichloroethyl, (−)-menthol, (−)-α-methylbenzyl, or other acid stable protecting group.

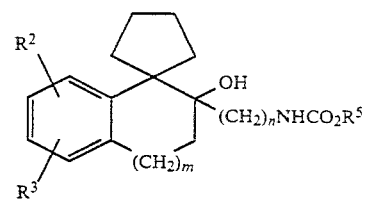

IX

Step (8) The compounds of the formula IX are treated with acetic acid, formic acid, triflouroacetic acid, sulfuric acid or the like or combinations thereof, preferably combinations of acetic acid and sulfuric acid to give the compounds of the formula X

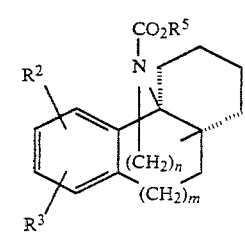

X

Step (9) The compounds of the formula X are treated to remove the carbamate functionalility using methods known to those skilled in the art for example wherein $R^5$ is 2,2,2-trichloroethyl the compounds are treated with zinc dust in methanol, ethanol or the like, in the presence of acetic acid, to afford the compounds of the formula I wherein n is 2 or 3, m is 0 or 1, $R^1$ is hydrogen and $R^2$ and $R^3$ are as previously defined.

Step (10) The compounds of the formula I wherein $R^1$ is hydrogen are treated with an aldehyde such as formaldehyde, acetaldehyde, benzaldehyde or the like or with a ketone such as acetone, acetophenone, or the like, in the presence of a reducing agent such as sodium cyanoborohydride or the like, in a solvent such as methanol, ethanol or the like to give the compounds of the formula I wherein n is 2 or 3, m is 0 or 1, $R^1$ is as previously defined excepting hydrogen, and $R^2$ and $R^3$ are as previously defined.

Step (11) Alternatively the compounds of the formula X are reduced in the presence of lithium aluminum hydride, diborane or the like, in a solvent such as ether, tetrahydrofuran or the like, to afford the compound of the formula I wherein $R^1$ is methyl.

Novel intermediates useful in the preparation of compounds of formula I are:

Spiro[cyclopentane-1,1'-[1H]inden]-2'(3'H)-one, 7,-methoxy-spiro[cyclopentane-1,1'-[1H]inden]-2'(3'H)-one, (+), (−), or (±)-3',4'-Dihydro-2'-hydroxyspiro[cyclopentane-1,1'(2'H)-napthalen]-2'-acetonitrile, (+), (−), or (±)-3',4'-dihydro-2'-hydroxy-7'-methoxyspiro[cyclopentane-1,1'(2'H)-napthalen]-2'-acetonitrile, (+), (−), or (±)-2',3'-Dihydro-2'-hydroxyspiro[cyclopentane-1,1'-[1H]inden]-2'-acetonitrile, (+), (−), or (±)-2',3'-Dihydro-2'-hydroxy-6-methoxyspiro[cyclopentane-1,1'-[1H]inden]-2'-acetonitrile, (+), (−), or (±)-2'-(2-aminoethyl)-3',4'-dihydrospiro[cyclopentane-1,1'(2H)-napthalen]-2'-ol, (+), (−), or (±)-2'-(2-aminoethyl)-3',4'-dihydro-7'-methoxyspiro[cyclopentane-1,1'(2'H)-napthalen]-2'-ol, (+), (−), or (±)-2'-(2-aminoethyl)-2',3',-dihydrospiro[cyclopentane-1,1'-[1H]inden-2'-ol, (+), (−), or (±)-2'-(2-aminoethyl)-2',3'-dihydro-6'-methoxyspiro[cyclopentane-1,1'-[1H]inden-2'-ol, Ethyl (+), (−), or (±)-[2-(3',4'-dihydro-2'-hydroxyspiro[cyclopentane-1,1'(2'H)-napthalen]-2'yl)ethyl]-carbamate, (+), (−), or (±)-2,2,2-Trichloroethyl-[2-(3',4'-dihydro-2'-hydroxyspiro[cyclopentane-1,1'(2'H)-naphthalen]-2'-yl)ethyl]carbamate, (+), (−, ) or (±)-2,2,2-Trichloroethyl-[2-(3',4'-dihydro-2'-hydroxy-7'-methoxyspiro[cyclopentane-1,1'(2'H)-naphthalen]-2'-yl)ethyl]carbamate, (+), (−), or (±)-2,2,2-Trichloroethyl-[2-[2',3'-dihydro-2'-hydroxyspiro[cyclopentane-1,1'-[1H]inden]-2'-yl)ethyl]carbamate, (+), (−), or (±)-2,2,2-Trichloroethyl-[2-2',3'-dihydro-2'-hydroxy-6'-methoxyspiro[cyclopentane-1,1'-[1H]inden]-2'-yl)ethyl]carbamate, Ethyl (+), (−), or (±)-2,3,4,5-tetrahydro-3a,9b-butano-1H-benz[g]indole-1-carboxylate, (+), (−), or (±)-2,2,2-Trichloroethyl-2,3,4,5-tetrahydro-3a,9b-butano-1H-benz[g]indole-1-carboxylate, (+), (−), or (±)-2,2,2-Trichloroethyl-2,3,4,5-tetrahydro-8-methoxy-3a,9b-butano-1H-benz[g]indole-1-carboxylate, (+), (−), or (±)-2,2,2-Trichloroethyl-2,3-dihydro-1H,4H-3a,8b-butanoindeno-[1,2-b]pyrrole-1-carboxylate, (+), (−), or (±)-2,2,2-Trichloroethyl-2,3-dihydro-7-methoxy-1H,4H-3a,8b-butanoindeno[1,2-b]pyrrole-1-carboxylate, (+), (−), or (±)-3',3'',4',4''Tetrahydrodispiro[cyclopentane-1,1'(2'H)-napthlene-2',2''(5''H)-furan]-5''-one, (+), (−), or (±)-3',3'',4',4''-Tetrahydro-7'-methoxydispiro[cyclopentane-1,1'(2'H)-napthlene-2',2''(5''H)-furan]-5''-one, (+), (−), or (±)-3'',4''-Dihydrodispiro-[cyclopentane-1,1'-[1H]indene-2'(3'H),2''(5''H)furan]-5''-one, (+), (−), or (±)-3'',4''-Dihydro-6'-methoxydispiro[cyclopentane-1,1'-[1H]indene-2'(3'H),2''(5''H)furan]-5''-one, (+), (−), or (±)-3',4'-Dihydro-2'-hydroxyspiro[cyclopentane-1,1'(2'H)-naphthalene]-2'-propanamide, (+), (−), or (±)-3',4'-Dihydro-2'-hydroxy-7'methoxyspiro[cyclopentane-1,1'(2'H)-naphthalene]-2'-propanamide, (+), (−), or (±)-2',3',-Dihydro-2'-hydroxyspiro[cyclopentane-1,1'-[1H]indene]-2'-propanamide, (+), (−), or (±)-2',3'-Dihydro-2'-hydroxy-6'-methoxyspiro[cyclopentane-1,1'-[1H]indene]-2'-propanamide, (+), (−), or (±)-2'-(3-aminopropyl)-3',4'-dihydrospiro[cyclopentane-1,1'(2'H)napthalen]-2'-ol, (+), (−), or (±)-2'-(3-aminopropyl)-3',4'-dihydro-7'-methoxyspiro[cyclopentane-1,1'(2'H)napthalen]-2'-ol, (+), (−), or (±)-2'-(3-aminopropyl)-2',3'-dihydrospiro[cyclopentane-1,1'-[1H]inden]-2'-ol , (+), (−), or (±)-2'-(3-aminopropyl)-2',3'-dihydro-6'-methoxyspiro[cyclopentane-1,1'-[1H]inden]-2'-ol, (+), (−), or (±)-2,2,2-Trichloroethyl-[3-(3',4'-dihydro-2'-hydroxyspiro[cyclopentane-1,1'(2'H)-napthalene]-2'-yl)propyl]carbamate, (+), (−), or (±)-2,2,2-Trichloroethyl-[3-(3',4'-dihydro-2'-hydroxy-7'-methoxyspiro[cyclopentane-1,1'(2'H)-napthlene]-2'-yl)propyl]carbamate, (+), (−), or (±)-2,2,2-Trichloroethyl-[3-(2',3'-dihydro-2'-hydroxyspiro[cyclopentane-1,1'-[1H]inden]-2'-yl)propyl]carbamate, (+), (−), or (±)-2,2,2-Trichloroethyl-[3-(2',3'-dihydro-2'-hydroxy-6'-methoxyspiro[cyclopentane-1,1'-[1H]inden]-2'-yl)-propyl]carbamate, (+), (−), or (±)-2,2,2-Trichloroethyl-3,4,5,6-tetrahydro-4a,10b-butanobenz[h]quinoline-1(2H)-carboxylate, (+), (−), or (±)-2,2,2-Trichloroethyl-3,4,5,6-tetrahydro-9-methoxy-4a,10b-butanobenz[h]quinoline-1(2H)-carboxylate, (+), (−), or (±)-2,2,2-Trichloroethyl-3,4-dihydro4a,9b-butano-5H-indeno[1,2-b]pyridine-1(2H)-carboxylate, and (+), (−), or (±)-2,2,2-Trichloroethyl-3,4-dihydro-8-methoxy-4a,9b-butano-5H-indeno[1,2-b]pyridine-1(2H)-carboxylate.

The compounds of the instant invention exhibit valuable pharmacological properties by selectively blocking the N-methyl-D-aspartate sensitive excitatory amino acid receptors in mammals. The compounds are thus useful for treating diseases responsive to excitatory amino acid blockade in mammals.

The effects are demonstrable in in vitro tests or in vivo animal tests using mammals or tissues or enzyme preparations thereof, e.g., mice, rats, or monkeys. The compounds are administered enterally or parenterally, for example, orally, transdermally, subcutaneously, intravenously, or intraperitoneally. Forms include but are not limited to gelatin capsules, or aqueous suspensions or solutions. The applied in vivo dosage may range between about 0.01 to 100 mg/kg, preferably between about 0.05 and 50 mg/kg, most preferably between about 0.1 and 10 mg/kg.

The ability of the compounds of the instant invention to interact with phencyclidine (PCP) receptors which represents a noncompetitive NMDA antagonist binding site, is shown by Examples 23 and 27 which bind with an affinity of less than 10 μM. Tritiated 1-[1-(2-thienyl)-cyclohexyl]pipiridine (TCP) binding, designated RBS1, was carried out essentially as described in *J. Pharmacol. Exp. Ther.* 238, 739 (1986).

For medical use, the amount required of a compound of formula I or pharmacologically acceptable salt thereof—(hereinafter referred to as the active ingredient) to achieve a therapeutic effect will, of course, vary both with the particular compound, the route of administration and the mammal under treatment and the particular disorder or disease concerned. A suitable systemic dose of a compound of formula I or pharmacologically acceptable salt thereof for a mammal suffering from, or likely to suffer from any condition as described herein before is in the range 0.01 to 100 mg of base per kilogram body weight, the most preferred dosage being 0.05 to 50 mg/kg of mammal body weight.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by intravenous infusion and repeated administrations, parenterally or orally, as considered appropriate.

While it is possible for an active ingredient to be administered alone, it is preferable to present it as a formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

Formulations suitable for parenteral administration conveniently comprise a sterile aqueous preparation of the active ingredient which is preferable isotonic with the blood of the recipient.

Formulations suitable for nasal or buccal administration (such as self-propelling powder dispensing formulations described hereinafter), may comprise 0.1 to 20% w/w, for example, 2% w/w of active ingredient.

The formulations, for human medical use, of the present invention comprise an active ingredient in association with a pharmaceuticaly acceptable carrier therefor and optionally other therapeutic ingredient(s). The carrier(s) must be 'acceptable' in the sense of being compatible with the other ingredients of the formulations and not deleterious to the recipient thereof.

So the pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose, and/or glycine; b) lubricants, e.g. silica, talcum, stearic acid, its magnesium or calcium salt, and/or polyethyleneglycol; for tablets also c) binders e.g. magnesium aluminum silicate, starch paste, gelatin, tragacanth, methylcellulose, sodium carboxymethylcellulose and/or polyvinylpyrrolidone; if desired d) disintegrants, e.g. starches, agar, alginic acid, or its sodium salt, or effervescent mixtures; and/or e) absorbents, colorants, flavors, and sweeteners. Injectable compositions are preferably aqueous isotonic solutions or suspensions, and suppositories are advantageously prepared from fatty emulsions, or suspensions. Said compositions may be sterilized and/or contain adjuvants, such as preserving, stabilizing, wetting or emulsifying agents, solution promoters, salts for regulating the osmotic pressure, and/or buffers. In addition, they may also contain other therapeutically valuable substances. Said compositions are prepared according to conventional mixing, granulating, or coating methods, respectively, and contain about 0.1 to 75%, preferably about 1 to 50%, of the active ingredient.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

The following examples are illustrative of the present invention but are not intended to limit it in any way.

EXAMPLE 1

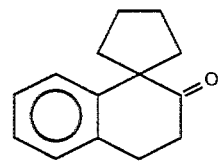

3′,4′-Dihydrospiro[cyclopentane-1,1′(2′H)-napthlen]-2′-one

A suspension of KOt-Bu (76.3 g, 0.68 mol) in 500 mL of xylene was treated dropwise with 2-tetralone (50 g, 0.34 mol). The resulting solution was treated dropwise with 1,4-dibromobutane (74.0 g, 0.34 mol) (exothermic reaction). The resulting suspension was heated to reflux for 18h. The reaction mixture was treated with water (200 mL) and the organic phase was collected. The aqueous phase was extracted with ethyl acetate (2×200 mL) and the combined organic extracts were dried (MgSO$_4$), filtered and concentrated. Distillation of the residue provided the product (65.6 g, 96%) as a colorless liquid.

EXAMPLE 2

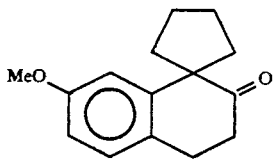

3',4'-Dihydro-7'-methoxyspiro-8 cyclopentane-1,1'(2'H)-napthlen]-2'-one

In a manner similar to that described in Example 1, 7-methoxy-2-tetralone (20.0 g, 0.113 mol) was converted to the title compound (10.3 g, 40%) as a colorless oil.

EXAMPLE 3

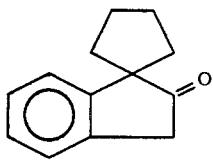

Spiro[cyclopentane-1,1'-[1H]inden]-2'(3'H)-one

In a manner similar to that described in Example 1, 2-indanone is converted to the title compound.

EXAMPLE 4

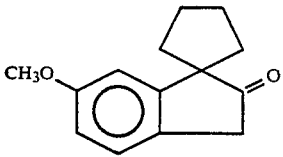

6'-Methoxy-spiro[cyclopentane-1,1'-[1H]inden]-2'(3'H)-one

In a manner similar to that described in Example 1, 5-methoxy-2-indanone is converted to the title compound.

EXAMPLE 5

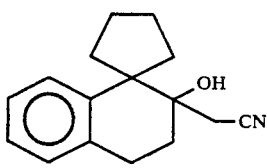

(±)-3',4'-Dihydro-2'-hydroxyspiro[cyclopentane-1,1'(2'H)-napthalen]-2'-acetonitrile A solution of acetonitrile (1.1 g, 27.5 mmol) in 100 mL of anhydrous tetrahydrofuran (THF) was cooled to −78° C. and treated with lithium diisopropylamide (18 mL of a 1.5 M solution in tetrahydrofuran). The resulting suspension was stirred at −78° C. for 30 minutes and treated dropwise with a solution of the product from Example 1 (5.0 g, 24.9 mmol) in 10 mL of anhydrous THF. The resulting solution was warmed to room temperature and saturated aq. NH$_4$Cl solution (15 mL) was added. The organic phase was collected and the aqueous phase was extracted with ether (3×50 mL). The combined organic phases were dried (MgSO$_4$, filtered and concentrated. The solid which formed was suspended in diisopropyl ether and collected by suction filtration. The material was dried under vacuum to give the title compound (4.14 g, 69%) as a white solid mp 165°–166° C.

Anal. (C$_{16}$H$_{19}$NO) Calc'd: C, 79.63; H, 7.94; N, 5.80 Found: C, 79.72; H, 7.86; N, 5.81

EXAMPLE 6

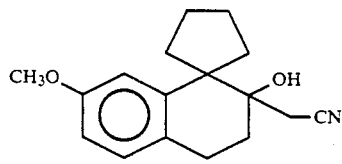

(±)-3',4'-Dihydro-2, hydroxy-7'-methoxyspiro[cyclopentane-1,1'(2'H)-napthalen]-2'-acetonitrile In a manner similar to that described in Example 5, the product of Example 2 (10.0 g, 43.4 mmol) was converted to the title compound (4.33 g, 37%) as a tan solid mp 126°–127° C.

Anal. (C$_{17}$H$_{21}$NO$_2$) Calc'd C, 75.25; H, 7.80; N, 5.16 Found: C, 75.36; H, 7.67; N, 4.94

EXAMPLE 7

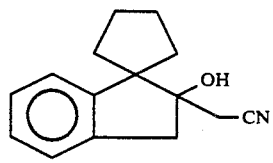

(±)-2',3'-Dihydro-2'-hydroxyspiro[cyclopentane-1,1'-[1H]inden]-2'-acetonitrile

In a manner similar to that described in Example 5, the product of Example 3 is converted to the title compound.

EXAMPLE 8

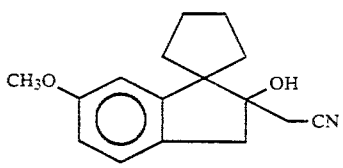

(±)-2',3'-Dihydro-2'-hydroxy-6-methoxyspiro[cyclopentane-1,1'-[1H]inden]-2'-acetonitrile In a manner similar to that described in Example 5, the product of Example 4 is converted to the title compound.

EXAMPLE 9

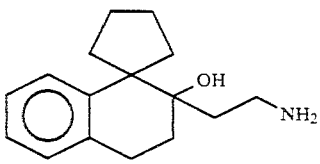

(±)-2'-(2-Aminoethyl)-3',4'-dihydrospiro[cyclopentane-1,1'(2'H)-napthalen]-2'-ol A solution of the product from Example 5 (2.50 g, 10.3 mmol) in 100 mL of methanolic ammonia was hydrogenated over Raney nickel (2.0 g) at 52 psi for 7.5 hours. The reaction mixture was filtered to remove the catalyst and the filtrate concentrated to give the title compound (2.59 g, quantitative) as a pale green solid mp 107°–109° C.

Anal. ($C_{16}H_{23}NO$) Calc'd: C, 79.63; H, 7.94; N, 5.81 Found: C, 79.37; H, 8.02; N, 5.59

EXAMPLE 10

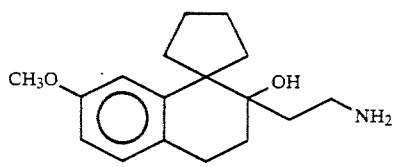

(±)-2'-(2-Aminoethyl)-3',4'-dihydro-7'-methoxyspiro[cyclopentane-1,1(2'H)-napthalen]-2'-ol In a manner similar to that described for Example 9, the product of Example 6 (4.85 g, 17.9 mmol) was hydrogenated to give the title compound (4.86 g, 99%) as a pale green solid.

Anal. ($C_{17}H_{25}NO_2$) Calc'd: C, 74.14; H, 9.15; N, 5.08 Found C, 73.40; H, 9.19; N, 5.04

EXAMPLE 11

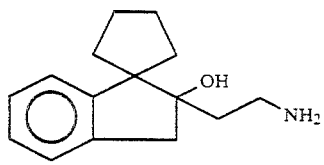

(±)-2'-(2-Aminoethyl)-2',3'-dihydrospiro[cyclopentane-1,1'-[1H]inden-2'-ol

In a manner similar to that described for Example 9, the product of Example 7 is hydrogenated to give the title compound.

EXAMPLE 12

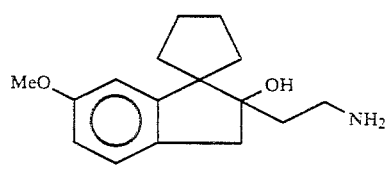

(±)-2'-(2-Aminoethyl)-2',3'-dihydro-6'-methoxyspiro-[cyclopentane-1,1'-[1H]inden-2'-ol In a manner similar to that described for Example 9, the product of Example 8 is hydrogenated to give the title compound.

EXAMPLE 13

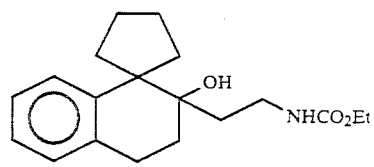

Ethyl (±)-[2-(3',4'-dihydro-2'-hydroxyspiro-[cyclopentane-1,1'(2'H)-napthalen]-2'-yl)ethyl]-carbamate A solution of the product from Example 9 (1.05 g, 4.28 mmol) and triethylamine (0.44 g, 4.35 mmol) in 10 mL of $CH_2Cl_2$ was cooled to 0° C. and ethyl chloroformate (0.47 g, 4.33 mmol) in 5 mL $CH_2Cl_2$ was added dropwise. The reaction was warmed to room temperature and washed with water. The aqueous phase was extracted with $CH_2Cl_2$ (3×20 mL) and the combined organic extracts were dried ($MgSO_4$), filtered and concentrated. The residue was purified by chromatography (silica gel, 1:1 heptane/ethyl acetate) to give the title compound (1.33 g, 98%) as an oil.

EXAMPLE 14

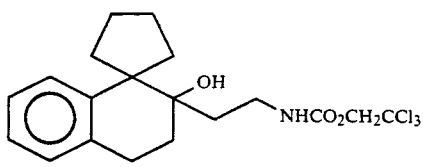

2,2,2-Trichloroethyl (±)-[2-(3',4'-dihydro-2'-hydroxyspiro-8 cyclopentane-1,1'(2'H)-naphthalen]-2'-yl)ethyl]carbamate A solution of the product from Example 9 (0.88 g, 3.59 mmol) and triethylamine (0.40 g, 3.78 mmol) in 10 mL of $CH_2Cl_2$ was cooled to 0° C. and treated dropwise with 2,2,2-trichloroethylchloroformate (0.80 g, 3.78 mmol) in 2 mL $CH_2Cl_2$. The resulting solution was stirred at 0° C. for 30 minutes and warmed to room temperature. The reaction mixture was washed with saturated aq. $NaHCO_3$ solution (10 mL). The aqueous phase was extracted with $CH_2Cl_2$ (10 mL). The combined organic extracts were dried ($MgSO_4$), filtered and concentrated. The residue was purified by chromatography (silica gel, 10:1 heptane/ethyl acetate) to give the title compound (1.18 g, 78%) as a viscous oil.

EXAMPLE 15

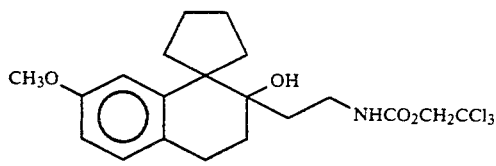

2,2,2-Trichloroethyl (±)-[2-(3',4'-dihydro-2'-hydroxy-7'-methoxyspiro[cyclopentane-1,1'(2'H)-naphthalen]-2'-yl)ethyl]carbamate In a manner similar to that described in Example 14, the product of Example 10 (4.66 g, 16.9 mmol) is converted to the title compound (6.81 g, as a foamy white solid.

EXAMPLE 16

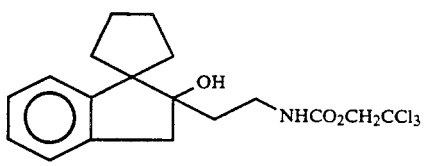

2,2,2-Trichloroethyl (±)-[2-[2',3'-dihydro-2'-hydroxy-spiro[cyclopentane-1,1'-[1H]inden]-2'-yl)ethyl]carbamate In a manner similar to that described in Example 14, the product of Example 11 is converted to the title compound.

EXAMPLE 17

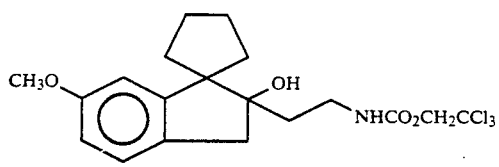

2,2,2-Trichloroethyl (±)-[2-[2',3'-dihydro-2'-hydroxy-6'-methoxyspiro[cyclopentane-1,1'-[1H]inden]-2'-yl)ethyl]carbamate In a manner similar to that described in Example 14, the product of Example 12 is converted to the title compound.

EXAMPLE 18

Ethyl (±)-2,3,4,5-tetrahydro-3a,9b-butano-1H-benz[g]indole-1-carboxylate

A solution of the product from Example 13 (1.68 g, 5.29 mmol) in 15 mL of 3:1 acetic acid/concentrated sulfuric acid (v/v) was stirred at room temperature for 18 hours. The reaction mixture was poured into water (50 mL) and the resulting mixture was extracted with $CH_2Cl_2$ (4×30 mL). The combined organic extracts were dried ($MgSO_4$), filtered and concentrated. The residue was dissolved in $CH_2Cl_2$ (100 mL and washed with saturated aq. bicarbonate solution (30 mL). The organic phase was dried ($MgSO_4$), filtered and concentrated. The residue was purified by chromatography (silica gel, 9:1 heptane/ethyl acetate) to give the title compound (0.94 g, 59%) as a white solid mp 67°-69° C.

Anal. ($C_{19}H_{25}NO_2$) Calc'd: C, 76 22; H, 8.42; N, 4.68 Found: C, 75.99; H, 8.38; N, 4.41

EXAMPLE 19

2,2,2-Trichloroethyl (±)-2,3,4,5-tetrahydro-3a,9b-butano-1H-benz[g]indole-1-carboxylate In a manner similar to that described in Example 18, the product of Example 14 (0.98 g, 2.33 mmol) was converted to the title compound (0.71 g, 76%) as an oil.

EXAMPLE 20

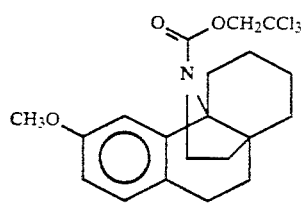

2,2,2-Trichloroethyl (±)-2,3,4,5-tetrahydro-8-methoxy-3a,9b-butano-1H-benz[g]indole-1-carboxylate In a manner similar to that described in Example 18, the product of Example 15 (5.16 g, 11.4 mmol) was converted to the title compound (4.18 g, 84%) as an oil.

EXAMPLE 21

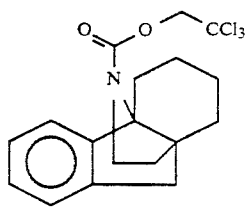

2,2,2-Trichloroethyl (±)-2,3-dihydro-1H,4H-3a,8b-butanoindeno[1,2-b]pyrrole-1-carboxylate In a manner similar to that described in Example 18, the product of Example 16 is converted to the title compound.

EXAMPLE 22

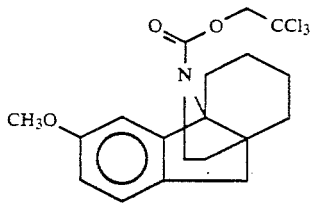

2,2,2-Trichloroethyl (±)-2,3-dihydro-7-methoxy-1H,4H-3a,8b-butanoindeno[1,2-b]pyrrole-1-carboxylate In a manner similar to that described in Example 18, the product of Example 17 is converted to the title compound.

EXAMPLE 23

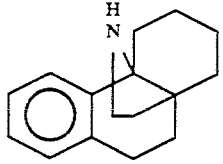

(±)-2,3,4,5-Tetrahydro-3a,9b-butano-1H-benz[g]indole hydrochloride

A solution of the product from Example 19 (0.70 g, 1.74 mmol) in 20 mL of methanol and 0.5 mL acetic acid was treated with zinc dust (1.58 g, 320 mesh) and the resulting suspension stirred at room temperature for three hours. The reaction mixture was filtered and the filtrate concentrated. The residue was dissolved in ether (30 mL) and extracted with aqueous 1N HCl (3×15 mL). The combined acid extracts are made basic (pH=11) with potassium carbonate and the resulting aqueous solution was extracted with $CH_2Cl_2$ (5×15 mL). The combined organic extracts were dried ($Na_2SO_4$, filtered and concentrated. The residue (0.30 g) was converted to its HCl salt by dissolution in ether and treatment with a saturated solution of HCl (gas) in ether. The solid which formed was collected by filtration and dried under vacuum (100° C.) to give the title compound (0.25 g, 54%) as a white solid mp >270° C.

Anal ($C_{16}H_{19}N.HCl$) Calc'd: C, 72.85; H, 8.40; N, 5.31; Cl, 13.44 Found: C, 72.66; H, 8.38, N, 4.98; Cl, 13.83

EXAMPLE 24

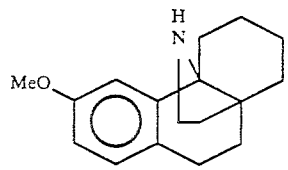

(±)-2,3,4,5-Tetrahydro-8-methoxy-3a,9b-butano-1H-benz[g]indole

In a manner similar to that described in Example 23, the product of Example 20 (3.76 g, 8.67 mmol) was converted to the title compound (1.47 g, 70%) as an oil. An analytical sample was prepared by crystallization of the fumarate salt from acetone which gave a white solid mp 203°–204° C.

Anal. ($C_{17}H_{23}NO.C_4H_4O_4$) Calc'd: C, 67.54; H, 7.29; N, 3.75 Found: C, 67.55; H, 7.18; N, 3.61

EXAMPLE 25

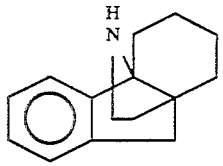

(±)-2,3-Dihydro-1H,4H-3a,8b-butanoindeno[1,2-b]pyrrole

In a manner similar to that described in Example 23, the product of Example 21 is converted to the title compound.

EXAMPLE 26

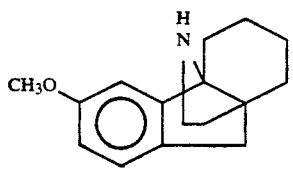

(±)-2,3-Dihydro-7-methoxy-1H,4H-3a,8b-butanoindeno-[1,2-b]pyrrole

In a manner similar to that described in Example 23, the product of Example 22 is converted to the title compound.

EXAMPLE 27

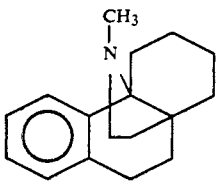

(±)-2,3,4,5-Tetrahydro-1-methyl-3a,9b-butano-1H-benz[g]indole hydrochloride

A solution of the product from Example 18 (0.77 g, 2.56 mmol) in 5 mL of THF was added dropwise to a suspension of lithium aluminum hydride (0.76 g, 20.0 mmol) in 15 mL of THF. The reaction mixture was stirred at room temperature for 18 hours and then heated to reflux for 1 hour. The reaction mixture was cooled to room temperature and quenched by the addition of small portions of $Na_2SO_4$-$10H_2O$ until no further gas evolution was observed. The reaction mixture was filtered and the filtrate was concentrated. The residue was dissolved in ether and treated with a saturated solution of dry HCl in ether. The solid which formed was collected by suction filtration and dried under vacuum (100° C.) to give the product (0.51 g, 72%) as a white solid mp 241°-253° C.

Anal. ($C_{17}H_{23}N.HCl$) Calc'd: C, 73.49; H, 8.71; N, 5.04; Cl, 12.76 Found: C, 73.39; H, 8.73; N, 4.82; Cl, 13.16

EXAMPLE 28

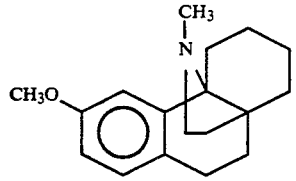

(±)-2,3,4,5-Tetrahydro-8-methoxy-1-methyl-3a,9b-butano-1H-benz[g]indole

A solution of the product from Example 24 (0.79 g, 3.08 mmol) and sodium cyanoborohydride (0.80 g, 12.7 mmol) in 10 mL methanol was treated dropwise with a 37% aqueous formalin solution (5 mL). The resulting solution was stirred at room temperature for 30 minutes, concentrated, and partitioned between 1N HCl (20 mL) and ether (20 mL). The organic phase was extracted with 1N HCl (2×10 mL) and the combined aqueous extracts were washed with ether. The aqueous phase was made basic with $K_2CO_3$ and extracted with $CH_2Cl_2$ (3×20 mL). The combined organic extracts were dried $K_2CO_3$, filtered and concentrated to give the title compound (0.87 g, quantitative) as a white solid mp 100°-102° C.

Anal. ($C_{18}H_{25}NO$) Calc'd: C, 79.66; H, 9.29; N, 5.16 Found: C, 79.52; H, 9.53; N, 4.71

EXAMPLE 29

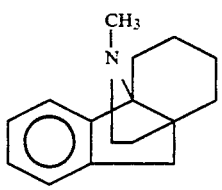

(±)-2,3-Dihydro-1-methyl-1H,4H-3a,8b-butanoindeno-[1,2-b]pyrrole

In a manner similar to that described in Example 28, the product of Example 25 is converted to the title compound.

EXAMPLE 30

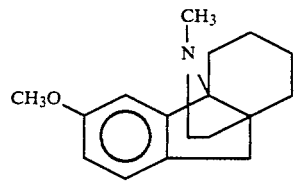

(±)-2,3-Dihydro-7-methoxy-1-methyl-1H,4H-3a,8b-butanoindeno[1,2-b]pyrrole

In a manner similar to that described in Example 28, the product of Example 26 is converted to the title compound.

EXAMPLE 31

(±)-2,3,4,5-Tetrahydro-1-ethyl-3a,9b-butano-1H-benz[g]indole fumarate

In a manner similar to that described in Example 28, the product from Example 23 (0.30 g, 1.32 mmol) and sodium cyanoborohydride (0.30 g, 4.77 mmol) was treated dropwise with acetaldehyde (0.20 g, 4.10 mmol) in 5 mL of methanol. Workup followed by crystallization of the fumarate salt from acetone gave the title compound (0.32 g, 65%) as a white solid mp 172°-173° C.

Anal. ($C_{18}H_{25}N.C_4H_4O_4$) Calc'd: C, 71 13; H, 7.87; N, 3.77 Found: C, 70.90: H, 7.79; N, 3.75

EXAMPLE 32

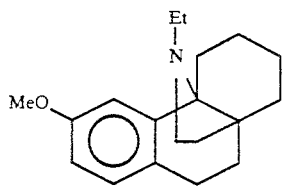

(±)-2,3,4,5-Tetrahydro-8-methoxy-1-ethyl-3a,9b-butano-1H-benz[g]indole hydrobromide In a manner similar to that described in Example 31, the product of Example 24 (0.27 g, 1.13 mmol) and acetaldehyde (0.32 g, 7.12 mmol) are reacted. Workup, followed by crystallization from ether and HBr gave the title compound (0.27 g, 64%) as a white solid mp 248°-251° C.

Anal. ($C_{19}H_{27}NO \cdot HBr$) Calc'd: C, 62.29; H, 7.71; N, 3.82; Br, 21.81 Found: C, 62.39; H, 7.65; N, 3.77; Br, 21.98

EXAMPLE 33

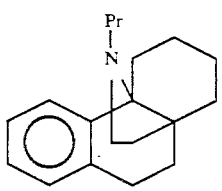

(±)-2,3,4,5-Tetrahydro-1-propyl-3a,9b-butano-1H-benz[g]indole hydrobromide

In a manner similar to that described in Example 32, the product from Example 23 (0.25 g, 1.10 mmol) and propionaldehyde (0.20 g, 3.47 mmol) was converted to the title compound (0.23 g, 60%) as a white solid mp 196°-198° C.

Anal. ($C_{19}H_{27}N \cdot HBr$) Calc'd: C, 64.92; H, 8.13; N, 4.07; Br, 23.09 Found C, 65.14; H, 8.06; N, 4.00; Br, 22.80

EXAMPLE 34

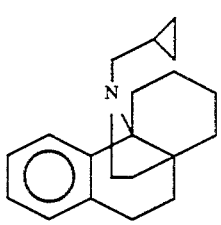

(±)-2,3,4,5-tetrahydro-1-(cyclopropylmethyl)-3a,9b-butano-1H-benz[g]indole fumarate In a manner similar to that described in Example 31, the product from Example 23 (0.25 g, 1.10 mmol) and cyclopropanecarboxaldehyde (0 23 g, 1.10 mmol) was converted to the title compound (0.26 g, 58%) as a white solid mp 150°-152° C.

Anal. ($C_{20}H_{27}N \cdot 1.2 \cdot C_4H_4O_4$) Calc'd: C, 70.80; H, 7.62; N, 3.33 Found: C, 71.05; H, 7.67, N, 3.32

EXAMPLE 35

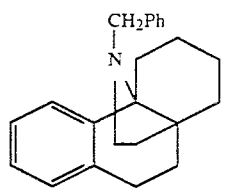

(±)-2,3,4,5-tetrahydro-1-phenylmethyl-3a,9b-butano-1H-benz[g]indole hydrochloride In a manner similar to that described in Example 32, the product from Example 23 (0.34 g, 1.50 mmol) and benzaldehyde are reacted. Workup, followed crystallization from ether and HCl gave the title compound (0 22 g, 42%) as a white solid mp 235-237° C.

Anal. ($C_{23}H_{27}N \cdot HCl$) Calc'd: C, 78.05; H, 7.98; N, 3.96; Cl, 10.02 Found: C, 77.60; H, 8.00, N, 3.34; Cl, 10.24

EXAMPLE 36

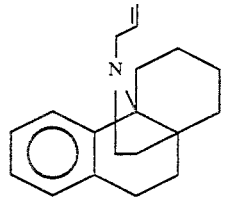

(±)-2,3,4,5-Tetrahydro-1-(2-propenyl)-3a,9b-butano-1H-benz[g]indole

In a manner similar to that described in Example 32, the product from Example 23 is converted to the title compound.

EXAMPLE 37

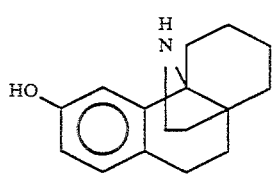

(±)-2,3,4,5-Tetrahydro-3a,9b-butano-1H-benz[g]indol-8-ol

A solution of the product from Example 24 is heated to reflux in 48% aqueous HBr until the starting material is consumed. The reaction mixture is poured into cold $NH_4OH$ solution and extracted into ethyl acetate. The combined organic extracts are dried ($Na_2SO_4$) and concentrated to give the title compound.

EXAMPLE 38

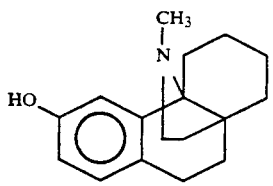

(±)-2,3,4,5-Tetrahydro-1-methyl-3a,9b-butano-1H-benz[g]indol-8-ol

In a manner similar to that described in Example 37, the product from Example 28 is converted to the title compound.

EXAMPLE 39

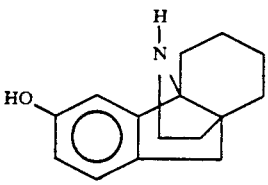

(±)-2,3-Dihydro-1H,4H-3a,8b-butanoindeno[1,2-b]pyrrol-7-ol

In a manner similar to that described in Example 37, the product from Example 26 is converted to the title compound.

EXAMPLE 40

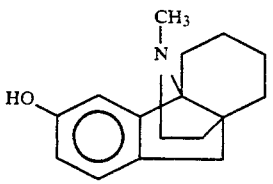

(±)-2,3-Dihydro-1-methyl-1H,4H-3a,8b-butanoindeno[1,2-b]-pyrrol-7-ol

In a manner similar to that described in Example 37, the product from Example 30 is converted to the title compound.

EXAMPLE 41

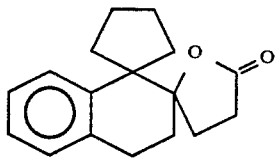

3',3'',4',4''-Tetrahydrodispiro[cyclopentane-1,1'(2'H)-napthlene-2',2''(5''H)-furan]-5''-one A solution of triethylsilyl N,N,N',N'-tetramethyl phosphoramidate (J. Amer. Chem. Soc. 1978, 100, 3468) (1.1 eq.) in anhydrous ether is cooled to 0° C. and treated with acrolein (1.0 eq.) in anhydrous ether. The resulting solution is stirred at 0° C. for 4.5 hours then cooled to −78° C. and a solution of n-butyllithium (1.0 eq.) is added. The resulting solution is treated with the product from Example 1 (1.0 eq.) and stirred at −78° C. for several hours. The reaction mixture is quenched with brine and extracted with several portions of ether. The combined extracts are dried and concentrated. The residue is dissolved in THF and cooled to 0° C. and tetra-n-butylammonium flouride (5 eq.) is added. The reaction mixture is warmed to room temperature and worked up as above to give the title compound.

EXAMPLE 42

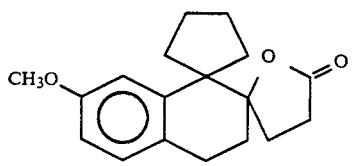

3',3'',4',4''-Tetrahydro-7,methoxydispiro-[cyclopentane-1,1'(2'H)-napthlene-2',2''(5''H)-furan1-5''-one In a manner similar to that described in Example 41, the product from Example 2 is converted to the title compound.

EXAMPLE 43

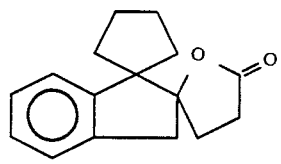

3'',4''-Dihydrodispiro[cyclopentane-1,1'-[1H]indene-2'(3'H),2''(5''H)-furan]-5''-one In a manner similar to that described in Example 41, the product from Example 3 is converted to the title compound.

EXAMPLE 44

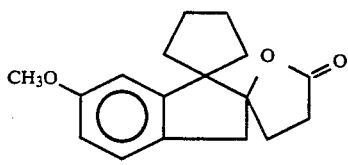

3'',4''-Dihydro-6'-methoxydispiro[cyclopentane-1,1'-[1H]indene-2'(3'H),2''(5''H)-furan]-5''-one In a manner similar to that described in Example 41, the product from Example 4 is converted to the title compound.

EXAMPLE 45

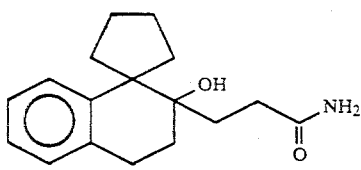

(±)-3′,4′-Dihydro-2′-hydroxyspiro[cyclopentane-1,1′(2′H)-naphthalene]-2′-propanamide A solution of the product from Example 41 is placed in a high pressure reactor and dissolved in tetrahydrofuran. Ammonia is condensed into the solution and the reaction vessel is sealed and the reaction mixture is stirred at room temperature for approximately 24 hours. The reaction vessel is vented and the remaining solvent is concentrated to give the title compound.

EXAMPLE 46

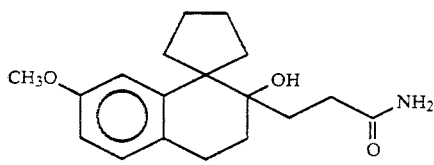

(±)-3′,4′-Dihydro-2′-hydroxy-7′-methoxyspiro-[cyclopentane-1,1′(2′H)-naphthalene]-2′-propanamide In a manner similar to that described in Example 45, the product from Example 42 is converted to the title compound.

EXAMPLE 47

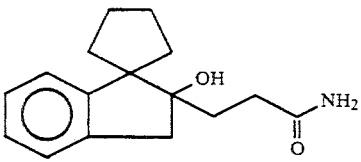

(±)-2′,3′-Dihydro-2′-hydroxyspiro[cyclopentane-1,1′-[1H]indene]-2′-propanamide

In a manner similar to that described in Example 45, the product from Example 43 is converted to the title compound.

EXAMPLE 48

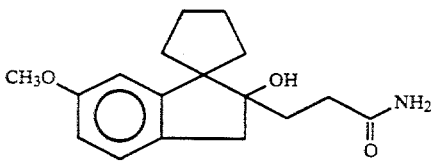

(±)-2′,3,-Dihydro-2′-hydroxy-6′-methoxyspiro[cyclopentane-1,1′-[1H]indene]-2′-propanamide In a manner similar to that described in Example 45, the product from Example 44 is converted to the title compound.

EXAMPLE 49

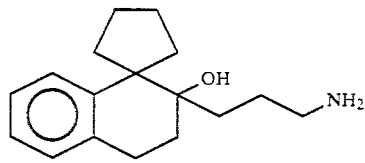

(±)-2′-(3-Aminopropyl)-3′,4′-dihydrospiro[cyclopentane-1,1′(2′H)napthalen]-2′-ol A solution of the product from Example 45, in tetrahydrofuran (THF) is added dropwise to a suspension of lithium aluminumhydride in THF. The resulting suspension is heated to reflux for 1 hour and then stirred at room temperature for 18 hours. The reaction mixture is quenched by the addition of small portions of $Na_2SO_4 \cdot 10H_2O$ until no more gas evolution is observed. The resulting suspension is filtered and the filtrate is concentrated to give the title compound.

EXAMPLE 50

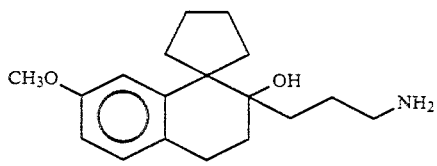

(±)-2′-(3-Aminopropyl)-3′,4′-dihydro-7′,-methoxyspiro[cyclopentane-1,1′(2′H)napthalen]-2′-ol In a manner similar to that described in Example 49, the product from Example 46 is converted to the title compound.

EXAMPLE 51

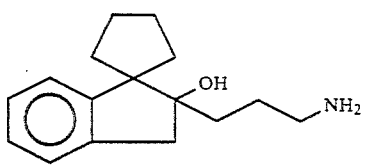

(±)-2′-(3-Aminopropyl)-2′,3′-dihydrospiro-[cyclopentane-1,1′-[1H]inden]-2′-ol

In a manner similar to that described in Example 49, the product from Example 47 is converted to the title compound.

EXAMPLE 52

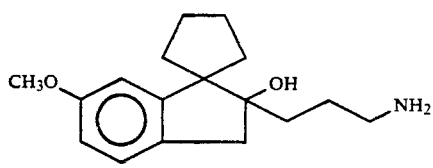

(±)-2'-(3-Aminopropyl)-2',3'-dihydro-6'-methoxyspiro[cyclopentane-1,1'(2',H)-NAPTHLENE]-2'-yl)propyl]carbamate In a manner similar to that described in Example 49, the product from Example 48 is converted to the title compound.

EXAMPLE 53

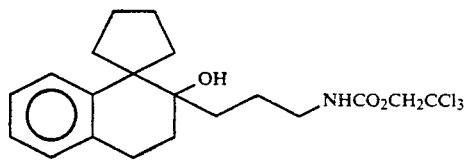

2,2,2-Trichloroethyl (±)-[3-(3',4'-dihydro-2'-hydroxyspiro[cyclopentane-1,1'(2'H)-napthlene]-2'-yl)propyl[carbamate A solution of the product from Example 49 (1.0 eq.) and triethylamine (1.1 eq.) in $CH_2Cl_2$ is cooled to 0° C. and a solution of 2,2,2-trichloroethylchloroformate (1.1 eq.) in $CH_2Cl_2$ is added dropwise. The resulting solution is stirred at 0° C. for 30 minutes and warmed to room temperature. The reaction mixture is washed with bicarbonate, dried and concentrated t give the title compound.

EXAMPLE 54

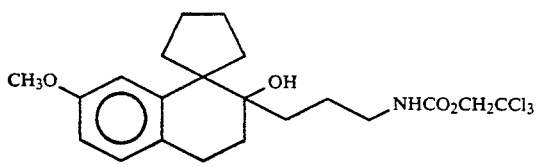

2,2,2-Trichloroethyl (±)-[3-(3',4'-dihydro-2'-hydroxy-7'-methoxyspiro[cyclopentane-1,1'(2'H)napthlene]-2'-yl)propyl]carbamate In a manner similar to that described in Example 53, the product from Example 50 is converted to the title compound.

EXAMPLE 55

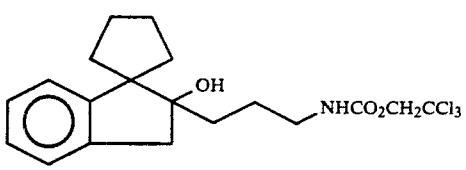

2,2,2-Trichloroethyl (±)-[3-(2',3'-dihydro-2'-hydroxyspiro[cyclopentane-1,1'[1H]inden]-2'-yl)propyl]carbamate In a manner similar to that described in Example 53, the product from Example 51 is converted to the title compound.

EXAMPLE 56

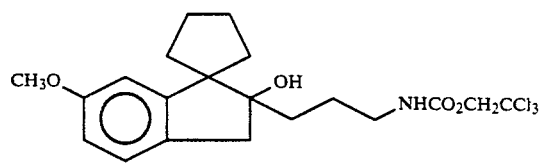

2,2,2-Trichloroethyl (±)-[3-(2',3'-dihydro-2'-hydroxy-6'-methoxyspiro[cyclopentane-1,1'[1H]inden]-2'-yl)propyl]carbamate In a manner similar to that described in Example 53, the product from Example 52 is converted to the title compound.

EXAMPLE 57

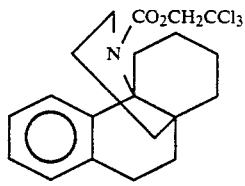

2,2,2-Trichloroethyl (±)-3,4,5,6-tetrahydro-4a,10b-butanobenz[h]quinoline-1(2H)-carboxylate In a manner similar to that described in Example 18, the product from Example 53 is converted to the title compound.

EXAMPLE 58

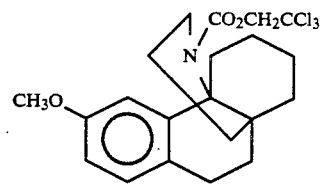

2,2,2-Trichloroethyl (±)-3,4,5,6-tetrahydro-9-4a,10b-butanobenz[h]quinoline-1(2H)-carboxylate In a manner similar to that described in Example 18, the product from Example 54 is converted to the title compound.

EXAMPLE 59

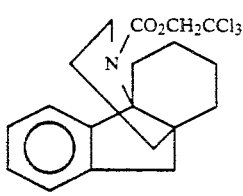

2,2,2-Trichloroethyl (±)-3,4-dihydro-4a,9b-butano-5H-indeno[1,2-b]pyridine-1(2H)-carboxylate In a manner similar to that described in Example 18, the product from Example 55 is converted to the title compound.

EXAMPLE 60

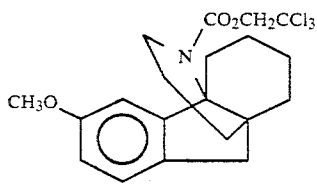

2,2,2-Trichloroethyl (±)-3,4-dihydro-8-methoxy-4a,9b-butano-5H-indeno[1,2-b]pyridine-1(2H)-carboxylate In a manner similar to that described in Example 18, the product from Example 56 is converted to the title compound.

EXAMPLE 61

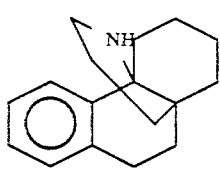

(±)-1,2,3,4,5,6-Hexahydro-4a,10b-butanobenz[h]quinoline

In a manner similar to that described in Example 23, the product from Example 57 is converted to the title compound.

EXAMPLE 62

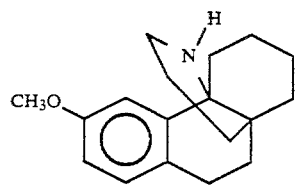

(±)-1,2,3,4,5,6-Hexahydro-9-methoxy-4a,10b-butanobenz[h]-quinoline

In a manner similar to that described in Example 23, the product from Example 58 is converted to the title compound.

EXAMPLE 63

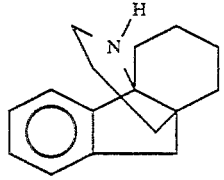

(±)-1,2,3,4-Tetrahydro-4a,9b-butano-5H-indeno[1,2-b]pyridine

In a manner similar to that described in Example 23, the product from Example 59 is converted to the title compound.

EXAMPLE 64

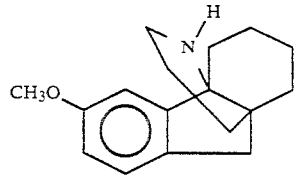

(±)-1,2,3,4-Tetrahydro-8-methoxy-4a,9b-butano-5H-indeno[1,2-b]pyridine

In a manner similar to that described in Example 23, the product from Example 60 is converted to the title compound.

EXAMPLE 65

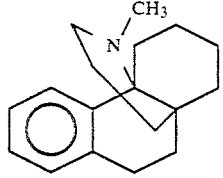

(±)-1,2,3,4,5,6-Hexahydro-1-methyl-4a,10b-butanobenz[h]quinoline

In a manner similar to that described in Example 28, the product from Example 61 is converted to the title compound.

EXAMPLE 66

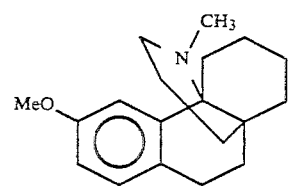

(±)-1,2,3,4,5,6-Hexahydro-9-methoxy-1-methyl-4a,10b-butanobenz[h]quinoline

In a manner similar to that described in Example 28, the product from Example 62 is converted to the title compound.

EXAMPLE 67

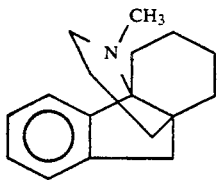

(±)-1,2,3,4-Tetrahydro-1-methyl-4a,9b-butano-5H-indeno[1,2-b]pyridine

In a manner similar to that described in Example 28, the product from Example 63 is converted to the title compound.

EXAMPLE 68

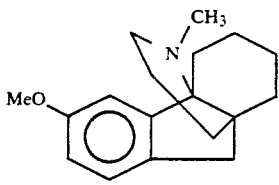

(±)-1,2,3,4-Tetrahydro-8-methoxy-1-methyl-4a,9b-butano-5H-indeno[1,2-b]pyridine

In a manner similar to that described in Example 28, the product from Example 64 is converted to the title compound.

EXAMPLE 69

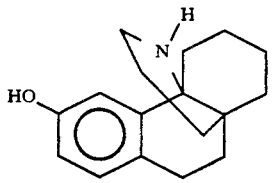

(±)-1,2,3,4,5,6-Hexahydro-4a,10b-butanobenz[h]quinolin-9-ol

In a manner similar to that described in Example 37, the product from Example 62 is converted to the title compound.

EXAMPLE 70

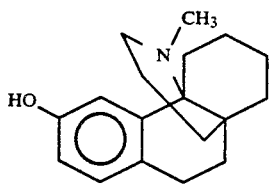

(±)-1,2,3,4,5,6-Hexahydro-1-methyl-4a,10b-butanobenz[h]quinoline-9-ol

In a manner similar to that described in Example 37, the product from Example 64 is converted to the title compound.

EXAMPLE 71

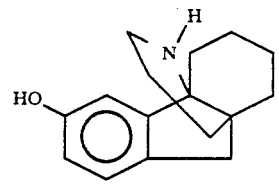

(±)-1,2,3,4-Tetrahydro-4a,9b-butano-5H-indeno[1,2-b]pyridin-8-ol

In a manner similar to that described in Example 37, the product from Example 66 is converted to the title compound.

EXAMPLE 72

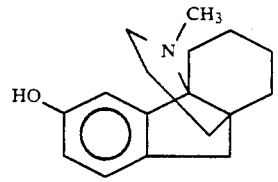

(±)-1,2,3,4-Tetrahydro-1-methyl-4a,9b-butano-5H-indeno[1,2-b]pyridin-8-ol

In a manner similar to that described in Example 37, the product from Example 68 is converted to the title compound.

I claim:
1. A compound of formula

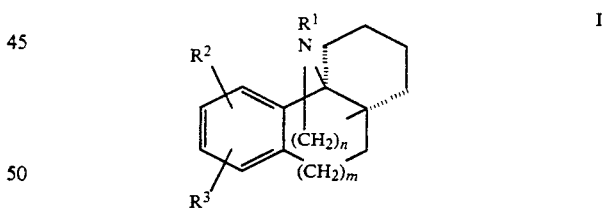

or a pharmaceutically acceptable acid addition salt thereof wherein:
$R^1$ is hydrogen, lower alkyl, lower alkenyl, lower alkynyl, arylloweralkyl, or cyclopropylloweralkyl,
$R^2$ and $R^3$ are each independently hydrogen, lower alkyl, hydroxy, lower alkoxy, halogen, amino, monoloweralkylamino or diloweralkylamino;
m is an integer of from 0 to 2; and
n is an integer of from 2 to 4.
2. A compound according to claim 1 wherein:
$R^1$ is hydrogen, lower alkyl, lower alkenyl, cyclopropylmethyl or arylloweralkyl;
$R^2$ and $R^3$ are each independently hydrogen, lower alkyl, hydroxy or lower alkoxy;
m is an integer 0 or 1; and
n is an integer 2 or 3.

3. A compound according to claim 1 wherein:
$R^1$ is hydrogen, lower alkyl, cyclopropylmethyl or arylloweralkyl;
$R^2$ and $R^3$ are each independently hydrogen, hydroxy or lower alkoxy; and
m is 0 or 1; and
n is 2 or 3.

4. A compound according to claim 1 wherein:
$R^1$ is hydrogen, methyl, ethyl, propyl, cyclopropylmethyl, or benzyl;
$R^2$ and $R^3$ are each independently hydrogen, methoxy, hydroxy;
m is the integer 0 or 1; and
n is the integer 2.

5. A compound selected from the list consisting of:
(+), (−), or (±)-2,3,4,5-Tetrahydro-3a,9b-butano-1H-benz[g]indole,
(+,(−), or (±)-2,3,4,5-Tetrahydro-1-methyl-3a,9b-butano-1H-benz[g]indole,
(+), (−), or (±)-2,3,4,5-Tetrahydro-1-ethyl-3a,9b-butano-1H-benz[g]indole,
(+), (−), or (±)-2,3,4,5-Tetrahydro-1-propyl-3a,9b-butano-1H-benz[g]indole,
(+), (−), or (±)-2,3,4,5-Tetrahydro-1-(cyclopropylmethyl)-3a,9b-butano-1H-benz[g]indole,
(+), (−), or (±)-2,3,4,5-Tetrahydro-1-phenylmethyl-3a,9b-butano-1H-benz[g]indole,
(+), (−), or (±)-2,3,4,5-Tetrahydro-8-methoxy-3a,9b-butano-1H-benz[g]indole,
(+), (−), or (±)-2,3,4,5-Tetrahydro-8-methoxy-1-methyl-3a,9b-butano-1H-benz[g]indole, and
(+), (−), or (±)-2,3,4,5-Tetrahydro-8-methoxy-1-ethyl-3a,9b-butano-1H-benz[g]-indole.

6. A pharmaceutical composition for treating cerebrovascular disorders comprising an amount effective for treating cerebrovascular disorders of a compound of claim 1 together with a pharmaceutically acceptable carrier.

7. A method of treating cerebrovascular disorders which comprises administering to a patient a pharmaceutical composition according to claim 1 in unit dosage form.

8. A method of anesthetizing a patient undergoing a surgical operation where risk of cerebrovascular damage exists which comprises administering to said patient a pharmaceutical composition according to claim 1 in unit dosage form.

* * * * *